US011191705B2

(12) United States Patent
Wang et al.

(10) Patent No.: US 11,191,705 B2
(45) Date of Patent: Dec. 7, 2021

(54) PERSONAL CLEANSING COMPOSITIONS

(71) Applicant: The Procter & Gamble Company, Cincinnati, OH (US)

(72) Inventors: Huan Wang, Singapore (SG); Ji-Quan Liu, Singapore (SG); Nadine Susanne Gallitschke-Irvine, Singapore (SG)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/125,940

(22) Filed: Sep. 10, 2018

(65) Prior Publication Data

US 2020/0078281 A1 Mar. 12, 2020

(51) Int. Cl.
*A61K 8/35* (2006.01)
*A61K 8/44* (2006.01)
*A61K 8/46* (2006.01)
*A61K 8/49* (2006.01)
*A61K 8/73* (2006.01)
*A61Q 17/00* (2006.01)
*A61Q 19/10* (2006.01)
*C11D 17/00* (2006.01)

(52) U.S. Cl.
CPC ............... *A61K 8/35* (2013.01); *A61K 8/442* (2013.01); *A61K 8/463* (2013.01); *A61K 8/4926* (2013.01); *A61K 8/732* (2013.01); *A61Q 17/005* (2013.01); *A61Q 19/10* (2013.01); *C11D 17/0047* (2013.01); *A61K 2800/524* (2013.01)

(58) Field of Classification Search
None
See application file for complete search history.

(56) References Cited

U.S. PATENT DOCUMENTS

| | | | | |
|---|---|---|---|---|
| 6,451,333 | B1 * | 9/2002 | Beerse | A61K 8/347 424/401 |
| 8,840,911 | B2 * | 9/2014 | Flugge-Berendes | A61K 8/86 424/411 |
| 9,050,288 | B2 | 6/2015 | Gilbard et al. | |
| 9,247,737 | B2 | 2/2016 | Cornmell | |
| 2004/0247551 | A1 | 12/2004 | Yokomaku | |
| 2005/0053572 | A1 | 3/2005 | Hwang | |
| 2014/0274852 | A1 | 9/2014 | Jiang et al. | |
| 2015/0173355 | A1 | 6/2015 | Konate | |
| 2017/0354177 | A1 | 12/2017 | Iohara | |
| 2018/0333339 | A1 | 11/2018 | Hamersky | |
| 2019/0000737 | A1 * | 1/2019 | Kelly | A01N 37/28 |
| 2021/0000724 | A1 | 1/2021 | Wang et al. | |

FOREIGN PATENT DOCUMENTS

| | | |
|---|---|---|
| FR | 2855564 B1 | 4/2007 |
| JP | H11269042 A | 10/1999 |
| JP | H11269043 A | 10/1999 |
| JP | 2003026546 A | 1/2003 |
| JP | 2006045126 A | 2/2006 |
| JP | 2007169233 A | 7/2007 |
| JP | 2011251923 A | 12/2011 |
| KR | 20000038214 A | 7/2000 |
| KR | 20070056207 A | 6/2007 |
| KR | 20070074690 A | 7/2007 |
| KR | 100782273 B1 | 12/2007 |
| KR | 101066797 B1 | 9/2011 |
| KR | 101114307 B1 | 2/2012 |
| WO | 2006134160 A2 | 12/2006 |

OTHER PUBLICATIONS

U.S. Appl. No. 16/022,863, filed Jun. 29, 2018, Casey Patrick Kelly et al.
International Search Report and Written Opinion of the International Searching Authority, PCT/US2019/047613, dated Nov. 21, 2019, 15 pages.
All final and non-final office actions for U.S. Appl. No. 16/919,415.
U.S. Appl. No. 16/919,415, filed Jul. 2, 2020, Wang et al.
PCT International Search Report and Written Opinion for PCT/US2020/070231 dated Oct. 23, 2020.

* cited by examiner

*Primary Examiner* — Patricia Duffy
*Assistant Examiner* — Garen Gotfredson
(74) *Attorney, Agent, or Firm* — Linda M. Sivik

(57) ABSTRACT

Cleansing compositions can include hinokitiol; and a 2-pyridinol N-oxide material; wherein the ratio by weight of the 2-pyridinol N-oxide material to the hinokitiol is about 1:4 to about 2:1 and the combination of the 2-pyridinol N-oxide material and hinokitiol includes about 9 ppm or more by weight of the cleansing composition.

13 Claims, No Drawings

PERSONAL CLEANSING COMPOSITIONS

FIELD OF THE INVENTION

The present application is directed to personal cleansing compositions containing a 2-pyridinol N-oxide material, like piroctone olamine, and hinokitiol and methods relating to 2-pyridinol N-oxide materials and hinokitiol.

BACKGROUND OF THE INVENTION

Personal cleansing compositions can contain antimicrobial materials as a preservative, as an agent to be applied to skin, or both. When these agents are used as preservatives, they are generally used at a relatively low amount as only small amounts are needed to preserve a product. The small weight percentage needed for efficacious preservation of a composition allows for the use of higher cost materials. However, when looking to use these materials as agents for application to the skin, higher levels of the materials are often needed so that an efficacious amount can be deposited on the skin. This is especially true where the material is to be deposited from a cleansing composition. If synergistic combinations of materials can be discovered, this can allow for the use of agents at lower levels and make a formulation more economically feasible.

SUMMARY OF THE INVENTION

A rinse-off cleansing composition comprising a soap, a surfactant, or a combination thereof; hinokitiol; and a 2-pyridinol N-oxide material; wherein the ratio by weight of the 2-pyridinol N-oxide material to the hinokitiol is about 1:4 to about 2:1 and the combination of the 2-pyridinol N-oxide material and hinokitiol comprise about 9 ppm or more by weight of the cleansing composition.

A method of potentiating a 2-pyridinol N-oxide material including adding about 3 ppm or more hinokitiol by weight of a composition, such that the ratio by weight of the composition of the 2-pyridinol N-oxide material to the hinokitiol is from about 1:4 to about 2:1.

A method of potentiating hinokitiol comprising adding about 6 ppm or more of a 2-pyridinol N-oxide material by weight, such that the ratio by weight of the 2-pyridinol N-oxide material to the hinokitiol is from about 1:4 to about 2:1.

Use of piroctone olamine to potentiate hinokitiol wherein the ratio by weight of the piroctone olamine to the hinokitiol is about 1:4 to about 2:1.

Use of hinokitiol to potentiate piroctone olamine wherein the ratio by weight of the piroctone olamine to the hinokitiol is about 1:4 to about 2:1.

A hand sanitizing composition, comprising an alcohol; hinokitiol; and a 2-pyridinol N-oxide material; wherein the ratio by weight of the 2-pyridinol N-oxide material to the hinokitiol is about 1:4 to about 2:1 and the combination of the 2-pyridinol N-oxide material and hinokitiol comprise about 9 ppm or more by weight of the cleansing composition.

These and other combinations, methods, and uses may be described in the detailed description below.

DETAILED DESCRIPTION OF THE INVENTION

Antimicrobial compounds can be used in consumer products for a variety of reasons. These materials, however, can be expensive to include in a product, especially when they need to be used at a level high enough to be efficacious once applied to the skin from a rinse-off product like soap. As such, products and methods are needed which allow for the use of these materials at lower levels while maintaining efficacy.

Two of such antimicrobial compounds are hinokitiol and 2-pyridinol N-oxide materials, like piroctone olamine. Hinokitiol is often used as a preservative in consumer products where the levels needed to prevent microbe growth are small. However, hinokitiol is a more expensive antimicrobial and needs to be used at higher levels in cleansing products in order to be efficaciously delivered to the skin. Because of its cost and relatively higher dosage for a functional benefit, its application can be limited.

One way to combat the issues of cost of a material is to combine it with a lower cost material. This can be complicated depending on whether the materials interact, what each of the materials target, whether they can complement one another, how much of each is needed for efficacy, etc. This is considered to be an additive interaction between the materials, i.e. where each is doing what one would expect based on their individual properties. Occasionally, when materials are added together the combination performs better than what would be expected based on the individual performances. This is considered a synergistic relationship. Synergy can be determined through the use of a Combinatorial Minimum Inhibitory Concentration ("cMIC") test. This can be used to determine the combinatorial effects of two chemicals on anti-bacterial activity in a tissue culture setting.

It has been discovered that there is a synergistic relationship between hinokitiol and a 2-pyridinol N-oxide material, piroctone olamine. cMIC testing was conducted utilizing *Staphylococcus aureus* as the bacteria. Table 1, below, shows the level of bacteria growth affected by hinokitiol, piroctone olamine, or the combination of the two. As can be seen in Table 1, the minimum inhibitory concentration (MIC) of piroctone olamine against *Staphylococcus aureus* is 12.5 ppm and 33.3 ppm for hinokitiol. When combined, they were efficacious at levels of 6.25 ppm piroctone olamine and only 3.13 ppm of hinokitiol. Thus, a benefit is seen where the combination of piroctone olamine and hinokitiol comprise about 9 ppm or more by weight of the cleansing composition. Thus, hinokitiol and piroctone olamine levels are reduced by 10.7 times (33.3/3.13) and 2 times (12.5/6.25), respectively. This data demonstrates that piroctone olamine potentiates the antibacterial efficacy of hinokitiol. Thus, combining piroctone olamine and hinokitiol allows for the use of less of each material and can reduce costs.

TABLE 1

| S. aureus | | Piroctone Olamine | | | | | | | |
|---|---|---|---|---|---|---|---|---|---|
| | ppm | 25 | 20 | 17.5 | 15 | 12.5 | 6.25 | 3.13 | 0 |
| Hinokitiol | 50 | 2 | 1 | 1 | 1 | 0 | 0 | 1 | 1 |
| | 42.5 | 2 | 1 | 1 | 1 | 1 | 1 | 1 | 2 |
| | 33.5 | 2 | 1 | 1 | 1 | 1 | 0 | 1 | 4 |
| | 25 | 2 | 1 | 1 | 1 | 1 | 1 | 1 | *17* |
| | 12.5 | 2 | 1 | 1 | 1 | 0 | 0 | *30* | *65* |
| | 6.25 | 1 | 1 | 1 | 1 | 1 | 0 | *79* | *103* |
| | 3.13 | 1 | 1 | 0 | 0 | 0 | 0 | *99* | *78* |
| | 0 | 2 | 1 | 1 | 1 | 1 | *46* | *94* | *100* |

* italicized values indicate bacteria grow and values equal to or higher than 10 mean growth and values less than 10 mean no growth The results of Table 1, which shows growth of *S. aureus* ATCC 6538 in the presence of hinokitiol, piroctone olamine, and their combination, are laid out with respect to weight ratios of the two materials in Table 2, below. As can be seen from Table 2, a synergistic benefit is observed when the ratio by weight of piroctone olamine to hinokitiol is from about 1:4 to about 2:1.

TABLE 2

| Piroctone olamine (ppm) | Hinokitiol (ppm) | Bacterial growth | Ratio of Piroctone Olamine vs. Hinokitiol |
|---|---|---|---|
| 0 | 33.5 | Yes | NA |
| 6.25 | 25.0 | No | 1:4 |
| 6.25 | 12.5 | No | 1:2 |
| 6.25 | 6.25 | No | 1:1 |
| 6.25 | 3.13 | No | 2:1 |
| 6.25 | 0 | Yes | NA |

In addition to looking at the cMIC for piroctone olamine and hinokitiol, testing was conducted on a bar soap formulation for its long-lasting efficacy against *Staphylococcus aureus* when the formulation contained a 1:1 ratio by weight of piroctone olamine to hinokitiol. This was done in accordance with the Long Lasting Efficacy Test (LET) Method outlined below in the Methods section.

The LET test measures the residual antibacterial efficacy of the deposited or partitioned antibacterial material on the skin against an opportunistic pathogen like *S. aureus*. When a bar soap formulation containing 0.1% by weight of piroctone olamine and 0.1% by weight of hinokitiol was tested using the LET method, the bar soap showed a log reduction of 1.00 four hours after wash, see Table 3. Thus, the benefit of the combination of materials is still seen when delivered from a product form.

TABLE 3

| | 0.1% Hinokitiol + 0.1% Piroctone olamine bar soap |
|---|---|
| LOG reduction | 1.00 |
| standard error | 0.02 |
| p value | <0.0001 |

The synergistic combination of piroctone olamine and hinokitiol can be used as a standalone antimicrobial composition, which may or may not include a carrier material, or these materials may be added to other formulations through which these materials may be delivered to a situs, like skin.

Skin Cleansing Composition

One example of a composition into which a 2-pyridinol N-oxide material, like piroctone olamine, and hinokitiol may be placed is a skin cleansing composition. A skin cleansing composition may be a rinse-off composition or a leave-on composition. Rinse-off compositions are generally rinsed from the skin within seconds to minutes of applications, while leave-on compositions are intended to be left on the skin for an extended period of time, like hours to days. A skin cleansing composition can include, for example, from about 3 ppm to about 0.5%, by weight of the cleansing composition, of hinokitiol. It may also include from about 6 ppm to about 1%, by weight of the cleansing composition, of a 2-pyridinol N-oxide material, like piroctone olamine. The ratio by weight of a 2-pyridinol N-oxide material, like piroctone olamine, to hinokitiol can be, for example, from about 1:4 to about 2:1. The combination of the 2-pyridinol N-oxide material and hinokitiol comprise about 9 ppm, about 12 ppm, or about 15 ppm, or more, by weight of the cleansing composition.

A skin cleansing composition may contain a 2-pyridinol N-oxide material. 2-Pyridinol-N-oxide materials suitable for use herein can include a substituted or unsubstituted 2-pyridinol-N-oxide material or a salt thereof. Also included herein are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

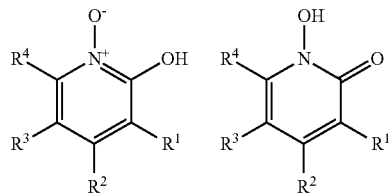

where $R^1$, $R^2$, $R^3$, $R^4$ groups are independently selected from the group consisting of H, Cl, Br, I, F, NO, $NO_2$, and $(CH_2)_n G$, where each G is independently selected from the group consisting of $(O)_m SO_3 M^3$, $(O)_m CO_2 M^3$, $(O)_m C(O)(R^5)$, $(O)_m C(O)N(R^5 R^6)$, $(O)_m CN$, $(O)_m (R^5)$, and $N(R^5 R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $^+N(R^7 R^8 R^9 R^{10})$, and $1/q\ M'^{q+}$ where M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_n G$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

The 2-pyridinol-N-oxide material may be a 2-pyridinol-N-oxide material or tautomer thereof according to the formula(s) above, where $R^1$, $R^2$, $R^3$, $R^4$ are independently selected from the group consisting of H, Cl, and $(CH_2)_n G$, where G is independently selected from the group consisting of $(O)_m SO_3 M^3$, $(O)_m CO_2 M^3$, $(O)_m C(O)(R^5)$, $(O)_m CN$, and $(O)_m (R^5)$, where m is 0 or 1.

The 2-pyridinol-N-oxide material may be a 2-pyridinol-N-oxide material according to the formula above, where $R^1$, $R^2$, $R^3$, $R^4$ are independently selected from the group consisting of H, $SO_3 M^3$, and $CO_2 M^3$. In still other aspects, $R^1$, $R^2$, $R^3$, $R^4$ are independently selected from the group consisting of H, $SO_3 M^3$, and $CO_2 M^3$, where no more than one $R^1$, $R^2$, $R^3$, $R^4$ is $SO_3 M^3$ or $CO_2 M^3$.

The 2-pyridinol-N-oxide material may be the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, ½ $Mg^{2+}$, or ½ $Ca^{2+}$, substituted ammonium, such as $C_1$-$C_6$ alkanolammonium, mono-ethanolamine (MEA), tri-ethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

The 2-pyridinol-N-oxide material may be of a substituted or unsubstituted 2-pyridinol-N-oxide material. Salts for use herein include those formed from the polyvalent metals barium, bismuth, strontium, copper, zinc, cadmium, zirconium, and mixtures thereof.

The 2-pyridinol-N-oxide material may be selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, Mo.) and/or Aces Pharma (Branford, Conn.).

The 2-pyridinol-N-oxide material may be a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

The 2-pyridinol-N-oxide material may be a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, Mo.), Princeton Building Blocks (Monmouth Junction, N.J.), 3B Scientific Corporation (Libertyville, Ill.), SynFine Research (Richmond Hill, ON), Ryan Scientific, Inc. (Mt. Pleasant, S.C.), and/or Aces Pharma (Branford, Conn.).

The 2-pyridinol-N-oxide material may be a 2-pyridinol-N-oxide material or tautomer thereof according to the formula(s) below:

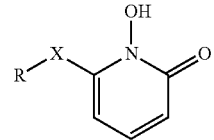

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

The 2-pyridinol-N-oxide material may be a 2-pyridinol-N-oxide material or tautomer thereof according to the formula(s) below:

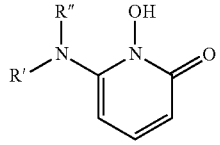

wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N-oxide material is 1-Hydroxy-4-methyl-6-(2,4,4-trimethylpentyl)-2-pyridone monoethanolamine salt.

As noted above, the 2-pyridinol-N-oxide material can comprise piroctone olamine.

As discussed herein, a skin cleansing composition may be, for example, in a liquid, solid, or semi-solid form. Solid compositions can take many forms like powder, pellets, bars, etc. These forms will generally be described herein as bar soap, but solid compositions could be in another form or shape. One example of a bar soap can include from about 0.1% to about 35%, by weight of the skin cleansing composition, of water, from about 45% to about 99%, by weight of the skin cleansing composition, of soap, and from about 0.01% to about 5%, by weight of the skin cleansing composition, of a particulate antimicrobial agent. Another suitable bar soap can include, for example, from about 0.1% to about 30%, by weight of the skin cleansing composition, of water, from about 40% to about 99%, by weight of the skin cleansing composition, of soap, and from about 0.25% to about 3%, by weight of the skin cleansing composition, of an antimicrobial agent.

Bar soap compositions can be referred to as conventional solid (i.e. non-flowing) bar soap compositions. Some bar soap compositions comprise convention soap, while others contain synthetic surfactants, and still others contain a mix of soap and synthetic surfactant. Bar compositions may include, for example, from about 0% to about 95% of a surfactant or from about 20% to about 95% of a surfactant. In one example, a bar soap composition may include, from about 0% to about 45% of a synthetic anionic surfactant. An example of a suitable conventional soap can include milled toilet bars that are unbuilt (i.e. include about 5% or less of a water-soluble surfactancy builder).

A skin cleansing bar composition can include, for example from about 45% to about 99% or from about 50% to about 75%, by weight of the skin cleansing composition, of soap, synthetic surfactant, or a combination thereof. Such soaps can include a typical soap, i.e., an alkali metal or alkanol ammonium salt of an alkane- or alkene monocarboxylic acid. Sodium, magnesium, potassium, calcium, mono-, di- and tri-ethanol ammonium cations, or combinations thereof, can be suitable for a skin cleansing composition. The soap included in a skin cleansing composition can include sodium soaps, from about 1% to about 25% ammonium, potassium, magnesium, calcium, or a mixture of these soaps. Additionally, the soap can be a well-known alkali metal salt of alkanoic or alkenoic acids having from about 8 to about 22 carbon atoms or from about 8 to about 18 carbon atoms. Another suitable soap can be alkali metal carboxylates of alkyl or alkene hydrocarbons having from about 12 to about 22 carbon atoms.

A skin cleansing composition can also include soaps having a fatty acid. For example, a bar soap composition could use from about 40% to about 95% of soluble alkali metal soap of $C_8$-$C_{24}$ or $C_{10}$-$C_{20}$ fatty acids. The fatty acid may, for example, have a distribution of coconut oil that can provide a lower end of a broad molecular weight range or a fatty acid distribution of peanut or rapeseed oil, or their hydrogenated derivatives, which can provide an upper end of the broad molecular weight range. Other such compositions can include a fatty acid distribution of tallow and/or vegetable oil. The tallow can include fatty acid mixtures that can typically have an approximate carbon chain length distribution of 2.5% $C_{14}$, 29% $C_{16}$, 23% $C_{18}$, 2% palmitoleic, 41.5% oleic, and 3% linoleic. The tallow can also include other mixtures with a similar distribution, such as fatty acids derived from various animal tallows and/or lard. In one example, the tallow can also be hardened (i.e., hydrogenated) such that some or all unsaturated fatty acid moieties can be converted to saturated fatty acid moieties.

Suitable examples of vegetable oil include palm oil, coconut oil, palm kernel oil, palm oil stearine, soybean oil, and hydrogenated rice bran oil, or mixtures thereof. One example of a suitable coconut oil can include a proportion of fatty acids having at least 12 carbon atoms of about 85%. Such a proportion can be greater when mixtures of coconut oil and fats such as tallow, palm oil, or non-tropical nut oils or fats can be used where principle chain lengths can be $C_{16}$ and higher. The soap included in a skin cleansing composition can be, for example, a sodium soap having a mixture of about 67-68% tallow, about 16-17% coconut oil, about 2% glycerin, and about 14% water.

Soap included in a skin cleansing composition can also be unsaturated in accordance with commercially acceptable standards. For example, a soap included in a skin cleansing composition could include unsaturation in a range of from about 37% to about 45% of saponified material.

Soaps included in a skin cleansing composition can be made, for example, by a classic kettle boiling process or modern continuous soap manufacturing processes wherein natural fats and oils such as tallow or coconut oil or their equivalents can be saponified with an alkali metal hydroxide using procedures well known to those skilled in the art. Soap can also be made by neutralizing fatty acids such as lauric ($C_{12}$), myristic ($C_{14}$), palmitic ($C_{16}$), or stearic ($C_{18}$) acids, with an alkali metal hydroxide or carbonate.

Soap included in a skin cleansing composition could also be made by a continuous soap manufacturing process. The soap could be processed into soap noodles via a vacuum flash drying process. One example of a suitable soap noodle comprises about 67.2% tallow soap, about 16.8% coconut soap, about 2% glycerin, and about 14% water, by weight of the soap noodle. The soap noodles can then be utilized in a milling process to finalize a skin cleansing composition.

Bar soap compositions can include fillers, such as starch, talc, sodium silicate, and combinations thereof. Fillers are often chemically inert materials used to modify the physical properties of the bar soap, like hardness. Fillers may be present at an amount of about 5% to about 30%, by weight of the skin cleansing composition. Starch for use herein, can include. For example, natural starch, such as an amylose or amylopectin containing starch, such as corn starch, wheat starch, rice starch, or other natural plant starch, which is not chemically modified.

Bar soap compositions can also include additional ingredients. These can include, for example, humectants, colorants, fragrances, thickeners, etc.

Examples of liquid cleansing compositions include, for example, body wash and hand soaps. These compositions can be single phase or multi-phase. The cleansing compositions can include surfactants. Surfactants are generally present in an amount of about 5% to about 50%. The surfactants can be, for example, linear, sulfate surfactants. Examples of such surfactants include sodium lauryl sulfate or ammonium lauryl sulfate in which these materials do not contain any ethoxylation or propoxylation. Additional surfactants include sodium laureth sulfate or ammonium laureth sulfate in which the materials contain a level of ethoxylation and/or propoxylation. Examples of such surfactants include sodium laureth-1 sulfate, sodium laureth-2 sulfate, sodium laureth-3 sulfate, ammonium laureth-1 sulfate, ammonium laureth-2 sulfate, or ammonium laureth-3 sulfate. Such materials can be described as SLEnS or ALEnS in which n is the average number of moles of ethoxylation and/or propoxylation.

The surfactant may also be a branched anionic surfactant. Examples of some suitable branched anionic surfactants include: sodium trideceth sulfate, sodium tridecyl sulfate, sodium $C_{12-13}$ alkyl sulfate, sodium $C_{12-15}$ alkyl sulfate, sodium $C_{11}$-15 alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, sodium $C_{12-14}$ pareth-n sulfate, and combinations thereof. Other salts of all the aforementioned surfactants are useful, such as TEA, DEA, ammonia, potassium, and sodium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, Tex.; from synthetic alcohols such as Neodol™ 23 Alcohol available from Shell Chemicals, USA; from synthetically made alcohols such as those described in U.S. Pat. No. 6,335,312 issued to Coffindaffer, et al. on Jan. 1, 2002. Suitable examples of alcohols are Safol™ 23 and Neodol™ 23. Suitable examples of alkoxylated alcohols are Safol™ 23-3 and Neodol™ 23-3. Sulfates can be prepared by conventional processes to high purity from a sulfur based $SO_3$ air stream process, chlorosulfonic acid process, sulfuric acid process, or Oleum process. Preparation via $SO_3$ air stream in a falling film reactor is an exemplary sulfonation process.

The surfactant may also be STnS, wherein n can define average moles of ethoxylation. A structured cleansing phase can include from about 5% to about 20%, from about 7% to about 18%, from about 5% to about 10%, from about 9% to about 16%, from about 11% to about 14%, by weight of the composition, of STnS, wherein n can range from about 0 to about 3, from about 0.5 to about 3, from about 1.1 to about 3.

Another anionic surfactant which can be used herein can is acyl glutamate. Acyl glutamate may have one or more of the following structures, in which R is an alkyl or alkenyl group (generally saturated although some may be unsaturated, for example, oleoyl, may be present) having 8 to 20 carbons and "$M^{30}$" is cation:

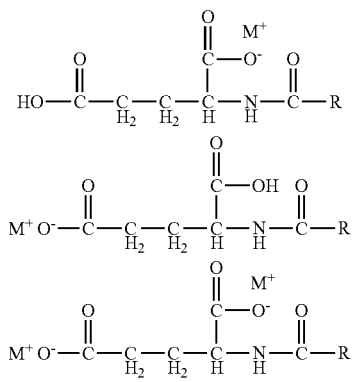

In one example, the acyl glutamate comprises a C10-C14 acyl glutamate. The acyl glutamate can have one or more cations selected from the group consisting of sodium, potassium, ammonium, substituted ammonium, and any combinations thereof.

In one aspect, the skin cleansing compositions comprise less than about 5% sodium lauryl sulfate (SLS), less than about 4% SLS, less than about 3% SLS, less than about 2% SLS, less than about 1% SLS, between about 0.1% SLS and about 2% SLS, or about 0% SLS.

The surfactant may also comprise cationic surfactants, nonionic surfactants, amphoteric surfactants, zwitterionic surfactants, and mixtures thereof. In one aspect, the composition comprises at least one amphoteric surfactant and/or at least one zwitterionic surfactant.

Amphoteric surfactants suitable for use herein can include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate, and N-higher alkyl aspartic acids. In one aspect, the composition can comprise an amphoteric surfactant that is selected from the group consisting of sodium lauroamphoacetate, sodium cocoamphoacetate, disodium lauroamphoacetate, disodium cocodiamphoacetate, and mixtures thereof. Moreover, amphoacetates and diamphoacetates can also be used.

Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the composition include betaines, including, for example, cocoamidopropyl betaine and laurylamidopropyl betaine.

Cationic surfactants can include those broadly described as surfactant with the surface-active portion bears a positive charge. The major classes of the cationics are a salt of long-chain amine or quaternary ammonium chloride or bromide. Examples of this class include behentrimonium chloride, benzalkonium chloride, benzethonium chloride, benzododecinium bromide, carbethopendecinium bromide, cetalkonium chloride, cetrimonium bromide, cetrimonium chloride, cetylpyridinium chloride, didecyldimethylammonium chloride, dimethyldioctadecylammonium bromide, dimethyldioctadecylammonium chloride, tetramethylammonium hydroxide, and mixtures thereof.

The nonionic surfactant may be, for example, an alkyl polyglycoside. Alkyl polyglycoside can have a structure as follows, in which "R" is an alkyl or alkenyl group (generally saturated although some may be unsaturated, for example oleoyl, may be present) having 8 to 20 carbons, and "m" is degree of polymerization which is typically 1 to 5:

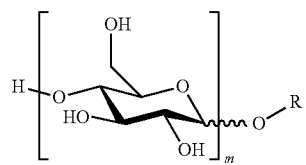

The skin cleansing composition may also comprise a combination of alkyl polyglycoside and acyl glutamate.

The cleansing composition may also comprise a structuring system wherein the structuring system can comprise an associative polymer, a non-associative polymer, an electrolyte, trihydroxystearin, and combinations thereof. The structuring system can comprise from about 0.05% to about 5%, from about 0.05% to about 1%, from about 0.07% to about 0.5%, or from about 0.1% to about 0.3%, by weight of the composition, of a structuring material such as a non-associative polymer. The structuring system can comprise from about 0.001% to about 5%, from about 0.005% to about 0.5%, from about 0.007% to about 0.05%, from about 0.008% to about 0.04%, or from about 0.01% to about 0.03%, by weight of composition, of an associative polymer. As noted herein, stability of a composition can be maintained or enhanced even with the reduction of associative polymer with the addition of a non-associative polymer. The composition may comprise from about 0.05% to about 5%, from about 0.05% to about 1% by weight of the composition, of a structuring material selected from the group consisting of an associative polymer, Trihydroxystearin, or combinations thereof.

An exemplary associative polymer can include AQUPEC® SER-300 made by Sumitomo Seika of Japan, which is an acrylate/$C_{10}$-$C_{30}$ alkyl acrylate cross-polymer and comprises stearyl side chains with less than about 1% hydrophobic modification. Associative polymers can comprise about $C_{16}$ (palmityl) alkyl hydrophobic side chains with about 0.7% hydrophobic modification, but a percentage hydrophobic modification can be up to an aqueous solubility limit in surfactant compositions (e.g., up to 2%, 5%, or 10%). Other associative polymers can include stearyl, octyl, decyl and lauryl side chains, alkyl acrylate polymers, polyacrylates, hydrophobically-modified polysaccharides, hydrophobically-modified urethanes, AQUPEC® SER-150 (acrylate/$C_{10}$-$C_{30}$ alkyl acrylate cross-polymer) comprising about $C_{18}$ (stearyl) side chains and about 0.4% HM, and AQUPEC® HV-701EDR which comprises about $C_8$ (octyl) side chains and about 3.5% HM, and mixtures thereof. Another exemplary associative polymer can be Stabylen 30 manufactured by 3V Sigma S.p.A., which has branched isodecanoate hydrophobic associative side chains.

As set forth above, the cleansing composition can further include a non-associative polymer. Suitable non-associative polymers can include water-dispersible polymers with relatively uniform hydrophilic backbone lacking hydrophobic groups. Examples of non-associative polymers can include biopolymer polysaccharides (e.g., xanthan gum, gellan gum), cellulosic polysaccharides (e.g., carboxymethyl cellulose, carboxymethyl hydroxyethyl cellulose), other polysaccharides (e.g., guar gum, hydroxypropyl guar, and sodium alginate), and synthetic hydrocarbon polymers (e.g., polyacrylamide and copolymers, polyethylene oxide, polyacrylic acid copolymers).

The cleansing composition may comprise from about 0.05% to about 10%, by weight of the composition, of an electrolyte. The electrolyte may comprise an anion selected from the group consisting of phosphate, chloride, sulfate, citrate, and mixtures thereof, and a cation selected from the group consisting of sodium, ammonium, potassium, magnesium, and mixtures thereof. The electrolyte may also be selected from the group consisting of sodium chloride, ammonium chloride, sodium sulfate, ammonium sulfate, and mixtures thereof.

The skin cleansing composition may comprise a dermatologically acceptable moisturizer. Such dermatologically acceptable moisturizers an include lipids of natural and/or petroleum based sources. Lipids of natural sources can include various vegetable oils such as soybean oil, coconut oil, palm oil, palm stearine oil, canola oil, sunflower oil, and corn oil. Other such natural lipids contain various plant and extract butters such as shea butter, cocoa butter. Petroleum sources oils contain petrolatum and various mineral oils.

The skin cleansing composition may comprise a dermatologically acceptable carrier. Dermatologically acceptable carriers may be selected for various stability, aesthetics, and/or compatibility with other materials present in the skin cleansing composition. Suitable carriers include water and/or water soluble solvents. The skin cleansing composition may comprise from about 1% to about 95% by weight of water and/or water equivalent solvent. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% water and/or a water-equivalent solvent. "Water-equivalent solvent" refers to a compound which has a similar ability as water to solubilize a material. Suitable water-equivalent solvents can include monohydric alcohols, dihydric alcohols, polyhydric alcohols, glycerol, glycols, polyalkylene glycols such as polyethylene glycol, and mixtures thereof. Particularly suitable solvents, include lower aliphatic alcohols such as ethanol, propanol, butanol, isopropanol; diols such as 1,2-propanediol, 1,3-propanediol, butanediol, pentanediol, hexanediol, heptanediol, octanediol, ethylhexanediol, decanediol; glycerin; water, and mixtures thereof. A skin cleansing composition can comprise, for example, water, a diol, glycerin, or combinations thereof.

Suitable carriers also include oils. The skin cleansing composition may comprise from about 1% to about 95% by weight of one or more oils. Oils may be used to solubilize, disperse, or carry materials that are not suitable for water or water-equivalent solvents. Suitable oils can include silicones, hydrocarbons, esters, fatty amides, ethers, and mixtures thereof. Oils may be fluid at room temperature. However, certain skin cleansing product forms (i.e., solid or semisolid) may require non-fluid oils. The oils may be volatile or nonvolatile. "Non-volatile" means a material that exhibits a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm Hg at 25° C. Volatile oils may be used to provide a lighter feel when a heavy, greasy film is undesirable.

Suitable oils include volatile oils. Volatile oils may have a viscosity ranging from about 0.5 to about 5 centistokes (cst) at 25° C. Volatile oils may be used to promote more rapid drying of the skin cleansing composition after it is applied to skin.

Non-volatile oils are also suitable for use in the composition. Non-volatile oils are often used for emolliency and protective properties. Non-volatile oils may have a viscosity ranging from about 5 cst to about 2,000,000 cst or from about 20 cst to about 200,000 cst.

Another example of a liquid cleansing composition is a hand sanitizer. A hand sanitizer is usually a leave on product. A hand sanitizer may comprise, for example, an alcohol, an antibacterial, a fragrance, surfactant, a colorant, beads, or any combination thereof. Alcohols for use herein can include, for example, ethanol, propanol, or a combination thereof. The alcohol may be present, for example, at a level of about 30% to about 80%, by weight of a hand sanitizing composition.

"Combinations:"

A. A rinse-off cleansing composition comprising a soap, a surfactant, or a combination thereof; hinokitiol; and a 2-pyridinol N-oxide material; wherein the ratio by weight of the 2-pyridinol N-oxide material to the hinokitiol is about 1:4 to about 2:1 and the combination of 2-pyridinol N-oxide material and hinokitiol comprise about 9 ppm or more by weight of the cleansing composition.

B. The rinse-off cleansing composition of paragraph A, wherein the composition comprises from about 3 ppm to about 0.5%, about 3 ppm to about 0.5%, about 3 ppm to about 0.4%, about 3 ppm to about 0.3%, about 3 ppm to about 0.2%, about 3 ppm to about 0.1%, about 3 ppm to about 0.05%, from about 3 ppm to about 0.01%, or from about 3 ppm to about 25 ppm, by weight of the cleansing composition, of the hinokitiol.

C. The rinse-off cleansing composition of any of paragraphs A-B, wherein the composition comprises from about 6 ppm to about 1%, about 6 ppm to about 0.75%, about 6 ppm to about 0.5%, about 6 ppm to about 0.4%, from about 6 ppm to about 0.3%, from about 6 ppm to about 0.2%, from about 6 ppm to about 0.1%, from about 6 ppm to about 0.05%, from about 6 ppm to about 0.01%, from about 6 ppm to about 50 ppm, or from about 20 ppm to about 50 ppm, by weight of the cleansing composition, of the 2-pyridinol N-oxide material.

D. The rinse-off cleansing composition of any of paragraphs A-C, wherein the 2-pyridinol N-oxide material comprises piroctone olamine E. The rinse-off cleansing composition of any of paragraphs A-D, wherein the rinse-off cleansing composition is a bar soap.

F. The rinse-off cleansing composition of paragraph E, wherein the composition comprises from about 65% to about 98%, by weight of the cleansing composition, of soap, a synthetic surfactant, or a combination thereof.

G. The rinse-off cleansing composition of any of paragraphs E-F, wherein the composition comprises from about 5% to about 30%, by weight of the composition, of a starch.

H. The rinse-off cleansing composition of any of paragraphs A-D, wherein the composition is a liquid cleansing composition.

I. A method of potentiating a 2-pyridinol N-oxide material comprising adding about 3 ppm or more hinokitiol by weight of a composition, such that the ratio by weight of the 2-pyridinol N-oxide material to the hinokitiol is from about 1:4 to about 2:1.

J. The method of paragraph I, wherein the combination of the hinokitiol and 2-pyridinol N-oxide material is at least 9 ppm, 12 ppm, or 15 ppm, by weight of the composition.

K. The method of any of paragraphs I-J, wherein the 2-pyridinol N-oxide material is present at a level of about 3 ppm to about 1%, by weight of the composition.

L. The method of any of paragraphs I-K, wherein the hinokitiol is present at a level of about 3 ppm to about 1%, about 3 ppm to about 0.75%, about 3 ppm to about 0.5%, about 3 ppm to about 0.4%, from about 3 ppm to about 0.3%, from about 3 ppm to about 0.2%, from about 3 ppm to about 0.1%, from about 3 ppm to about 0.05%, from about 3 ppm to about 0.01%, from about 3 ppm to about 50 ppm, or from about 20 ppm to about 50 ppm, by weight of the composition.

M. The method of any of paragraphs I-L, wherein the 2-pyridinol N-oxide material is present at a level of about 3 ppm to about 25 ppm by weight of the composition.

N. The method of any of paragraphs I-M, wherein the 2-pyridinol N-oxide material comprises piroctone olamine.

O. A method of potentiating hinokitiol comprising adding about 6 ppm or more of a 2-pyridinol N-oxide material by weight of a composition, such that the ratio by weight in the composition of the 2-pyridinol N-oxide material to the hinokitiol is from about 1:4 to about 2:1.

P. The method of paragraph 0, wherein the combination of the hinokitiol and 2-pyridinol N-oxide material is at least 9 ppm, 12 ppm, or 15 ppm, by weight of the composition.

Q. The method of any of paragraphs O-P, wherein the composition comprises from about 6 ppm to about 0.5%, about 6 ppm to about 0.5%, about 6 ppm to about 0.4%, about 6 ppm to about 0.3%, about 6 ppm to about 0.2%, about 6 ppm to about 0.1%, about 6 ppm to about 0.05%, from about 6 ppm to about 0.01%, or from about 6 ppm to about 25 ppm, by weight of the cleansing composition, of the 2-pyridinol N-oxide material.

R. The method of any of paragraphs O-Q, wherein the hinokitiol is present at a level of about 3 ppm to about 50 ppm by weight of the composition.

S. The method of any of paragraphs O-R, wherein the 2-pyridinol N-oxide material comprises piroctone olamine T. Use of piroctone olamine to potentiate hinokitiol wherein the ratio by weight of the piroctone olamine to the hinokitiol is about 1:4 to about 2:1, by weight of a composition.

U. The use of paragraph T, wherein the hinokitiol is present at a level of about 3 ppm or more, from about 3 ppm to about 0.5%, about 3 ppm to about 0.5%, about 3 ppm to about 0.4%, about 3 ppm to about 0.3%, about 3 ppm to about 0.2%, about 3 ppm to about 0.1%, about 3 ppm to about 0.05%, from about 3 ppm to about 0.01%, or from about 3 ppm to about 25 ppm, by weight of the composition.

V. The use of any of paragraphs T-U, wherein the piroctone olamine is present at a level of about 6 ppm or more, from about 6 ppm to about 1%, about 6 ppm to about 0.75%, about 6 ppm to about 0.5%, about 6 ppm to about 0.4%, from about 6 ppm to about 0.3%, from about 6 ppm to about 0.2%, from about 6 ppm to about 0.1%, from about 6 ppm to about 0.05%, from about 6 ppm to about 0.01%, from about 6 ppm to about 50 ppm, or from about 20 ppm to about 50 ppm, by weight of the composition.

W. The use of any of paragraphs T-V wherein the combination of piroctone olamine and hinokitiol comprise about 9 ppm or more by weight of the composition.

X. The use of any of paragraphs T-W, wherein the composition is a skin cleansing composition.

Y. Use of hinokitiol to potentiate piroctone olamine wherein the ratio by weight of the piroctone olamine to the hinokitiol is about 1:4 to about 2:1, by weight of a composition.

Z. The use of paragraph Y, wherein the piroctone olamine is present at a level of about 6 ppm or more, from about 6 ppm to about 1%, about 6 ppm to about 0.75%, about 6 ppm to about 0.5%, about 6 ppm to about 0.4%, from about 6 ppm to about 0.3%, from about 6 ppm to about 0.2%, from about 6 ppm to about 0.1%, from about 6 ppm to about 0.05%, from about 6 ppm to about 0.01%, from about 6 ppm to about 50 ppm, or from about 20 ppm to about 50 ppm, by weight of the composition.

AA. The use of any of paragraphs Y-Z, wherein the hinokitiol is present at a level of about 3 ppm or more, from about 3 ppm to about 0.5%, about 3 ppm to about 0.5%, about 3 ppm to about 0.4%, about 3 ppm to about 0.3%, about 3 ppm to about 0.2%, about 3 ppm to about 0.1%, about 3 ppm to about 0.05%, from about 3 ppm to about 0.01%, or from about 3 ppm to about 25 ppm, by weight of the composition.

BB. The use of any of paragraphs Y-AA, wherein the combination of piroctone olamine and hinokitiol comprise about 9 ppm or more by weight of the composition.

CC. The use of any of paragraphs Y-BB, wherein the composition is a skin cleansing composition.

DD. A hand sanitizer comprising hinokitiol; and a 2-pyridinol N-oxide material; wherein the ratio by weight of the 2-pyridinol N-oxide material to the hinokitiol is about 1:4 to about 2:1 and the combination of 2-pyridinol N-oxide material and hinokitiol comprise about 9 ppm or more by weight of the cleansing composition.

EE. The hand sanitizer of paragraph DD, comprising from about 3 ppm to about 0.5%, about 3 ppm to about 0.5%, about 3 ppm to about 0.4%, about 3 ppm to about 0.3%, about 3 ppm to about 0.2%, about 3 ppm to about 0.1%, about 3 ppm to about 0.05%, from about 3 ppm to about 0.01%, or from about 3 ppm to about 25 ppm, by weight of the composition, of hinokitiol.

FF. The hand sanitizer of any of paragraphs DD-EE, comprising from about 6 ppm to about 1%, about 6 ppm to about 0.75%, about 6 ppm to about 0.5%, about 6 ppm to about 0.4%, from about 6 ppm to about 0.3%, from about 6 ppm to about 0.2%, from about 6 ppm to about 0.1%, from about 6 ppm to about 0.05%, from about 6 ppm to about 0.01%, from about 6 ppm to about 50 ppm, or from about 20 ppm to about 50 ppm, by weight of the composition of the 2-pyridinol N-oxide material.

GG. The hand sanitizer of any of paragraphs DD-FF, wherein the 2-pyridinol N-oxide material comprises piroctone olamine HH. The hand sanitizer of any of paragraphs DD-GG, further comprising alcohol.

II. The hand sanitizer of paragraph HH, wherein the composition comprises from about 30% to about 80%, by weight of the composition, of the alcohol.

EXAMPLES

| Bar Soap Examples | | | | |
|---|---|---|---|---|
| Ingredient | Bar Ex. B1 | Bar Ex. B2 | Bar Ex. B3 | Bar Ex. B4 |
| Soap Noodle[a] | 74.58% | 78.00% | 77.58% | 75.00% |
| Piroctone olamine[b] | 0.10% | — | 0.10% | — |
| Hinokitiol[c] | — | 0.10% | 0.10% | — |
| Starch[d] | 20.00% | 20.00% | 20.00% | 20.00% |
| TiO$_2$[e] | 0.50% | 0.50% | 0.50% | 0.50% |
| Fragrance | 1.0% | 1.0% | 1.5% | 0.8% |
| Water | Q.S. to 100 | Q.S. to 100 | Q.S. to 100 | Q.S. to 100 |
| Moisture Loss | −1.00% | −1.00% | −1.00% | −1.00% |

[a]67.2% tallow soap, about 16.8% coconut soap, about 2% glycerin and about 14% water. These percentage amounts are by weight of the soap noodle;
[b]Piroctone Olamine sold by Clariant;
[c]Hinokitiol sold be Sigma-Aldrich;
[d]NATIONAL CHA501 sold by National Starch and Chemical
[e]MT-500B sold by Tayca Corporation The bar examples are made in accordance with standard bar processing. This can include, for example, agglomerating the listed ingredients in the sequence listed, roll-milling at least twice, plodding at least twice, and then stamping the example into a selected bar shape.

| Liquid Hand Cleanser Examples | | | |
|---|---|---|---|
| Ingredient | Liquid Hand Soap Ex. L1 | Comparative Liquid Soap Ex. L2 | Comparative Liquid Soap Ex. L3 |
| Sodium Laureth 3 Sulfate 28% solution[f] | 30.0% | 20.0% | 15.00% |
| Sodium Lauryl Sulfate 29% solution[g] | — | 5.0% | 3.0% |
| Cocoamidopropyl Betaine (30% active)[h] | 3.50% | 3.0% | 2.50% |
| Sodium Benzoate[i] | 0.45% | 0.45% | 0.45% |
| Methylchloroisothiazolinone/methylisothiazolinone[j] | 0.05% | 0.05% | 0.05% |
| EDTA[k] | 0.10% | 0.10% | 0.10% |
| Fragrance | 0.70% | 0.70% | 0.70% |
| Piroctone Olamine[l] | 0.1% | 0.2% | 0.2% |
| Hinokitiol[m] | 0.1% | 0.1% | 0.05% |
| Sodium Chloride[n] | 0-3% | 0-3% | 0-3% |
| Citric acid[o] | Adjust pH | Adjust pH | Adjust pH |
| Purified water | Q.S. to 100 | Q.S. to 100 | Q.S. to 100 |
| pH | 6.00 | 6.00 | 4.50 |

[f]SLE3S sold by Stepan company;
[g]SLS sold by Tianjin Tianzhi Fine Chemical Co.,Ltd;
[h]AMPHOSOL HCA-HP sold by Stepan;
[i]Sodium Benzoate ≥99%, FCG, FG sold by Sigma-Aldrich;
[j]Kathon CG sold by Dow Chemical;
[k]Obtained from Sigma Aldrich;
[l]Piroctone olamine sold by Clariant;
[m]Hinokitiol from Sigma-Aldrich;
[n]Adjust to desired viscosity;
[o]Citric acid ACS reagent, ≥99.5% sold by Sigma-Aldrich

| Body Wash Examples | | | |
|---|---|---|---|
| Ingredient | Body Wash Ex. W1 | Body Wash Ex. W2 | Body Wash Ex. W3 |
| Sodium Laureth 3 Sulfate 28% solution[f] | 35.0% | 20.0% | 18.00% |
| Sodium Lauryl Sulfate 29% solution[g] | — | 15.0% | 10.0% |
| Cocoamidopropyl Betaine (30% active)[h] | 5.0% | 3.0% | 3.50% |
| Sodium Benzoate[i] | 0.45% | 0.45% | 0.45% |
| Methylchloroisothiazolinone/methylisothiazolinone[j] | 0.05% | 0.05% | 0.05% |
| EDTA[k] | 0.10% | 0.10% | 0.10% |
| Fragrance | 0.70% | 0.70% | 0.70% |
| Piroctone Olamine[l] | 0.1% | 0.2% | 0.2% |
| Hinokitiol[m] | 0.1% | 0.1% | 0.05% |
| Sodium Chloride[n] | 0-3% | 0-3% | 0-3% |
| Citric acid[o] | Adjust pH | Adjust pH | Adjust pH |
| Purified water | Q.S. to 100 | Q.S. to 100 | Q.S. to 100 |
| pH | 7.0 | 7.0 | 7.0 |

The liquid hand soap and body wash examples are made by standard processes. This includes thoroughly mixing the ingredients until the appearance and viscosity of the example meets the desired result, for example, transparency and a viscosity of about 1 cps to about 30,000 cps.

| Hand Sanitizer Examples | | |
|---|---|---|
| Ingredient | Hand sanitizer Ex. HS1 | Hand sanitizer Ex. HS2 |
| Ethanol | 70.0% | 0 |
| Cetrimonium chloride | 0 | 0.2% |
| benzalkonium chloride | 0 | 0.1% |
| Fragrance | 0.50% | 0.50% |
| Piroctone Olamine | 0.1% | 0.1% |
| Hinokitiol | 0.1% | 0.05% |

-continued

Hand Sanitizer Examples

| Ingredient | Hand sanitizer Ex. HS1 | Hand sanitizer Ex. HS2 |
|---|---|---|
| Citric acid | Adjust pH | Adjust pH |
| Purified water | Q.S. to 100 | Q.S. to 100 |
| pH | 5.5 | 5.5 |

The hand sanitizer examples are made by standard processes. This includes thoroughly mixing the ingredients until the appearance and viscosity of the example meets the desired result, for example, transparency and a viscosity of about 0.01 cps to about 100 cps.

Method

LET Method (Ex-Vivo Long-Lasting Efficacy Test)

1.1. Test Organism Preparation

Refresh *S. aureus* ATCC 6538 by streaking on a Trypticase Soy Agar (TSA) plate and grow 18-24 hrs. On the second day, inoculate 1 bacterial colony in a 50 ml tube containing 30 ml Trypticase Soy Broth (TSB), and grow at 35±2° C. for 18 hours±15 min. One the test day, dilute the above bacteria culture by 1:50 to new TSB (e.g. 0.5 ml culture to 24.5 ml TSB media in a 50 ml tube), and grow at 35±2° C. with sharking at 200 rpm for 1-2.5 hr. The test organism culture may be used within half an hour to inoculating on to pig skin for all samples tested.

1.2. Washing of Pigskin 1.2.1. Maintain the tap water temperature 35±2° C., water flow rate 4.0±0.3 L/min throughout the washing process.

1.2.2. Pig skin size choice: for one microorganism test, cut the pig skin (~10 cm*15 cm) into halves (e.g. ~10 cm*7.5 cm), and use one of the half skin per test leg repeat;

1.2.3. Washing procedure:
  a) Rinse tissue with tap water from the clamped end for 15 sec. The angle between tap water to pig skin should be about 120 degrees.
  b) After rinse, place the pigskin hard board onto a flat surface. Rub the bar soap over the pigskin surface for 15 sec.
  c) Rub the tissue and lather for 45 sec. Ensure all parts were lathered consistently.
  d) Rinse the tissue with tap water from the clamped end for 15 sec.
  e) Blot dry the tissue gently with Kimwipes or paper towel. Place the pigskin hard board to a flat surface to air dry for at least 1 min.
  f) Repeat steps (b-e) to achieve nine times in total. Only after the final wash step e), unclamp the pigskin, hold the pigskin with gloved hands and briefly rinse the back of pig skin for about 2 sec to get rid of foams. Put the pigskin on top of Kimwipes or paper towel with pigskin pore pacing up. Blot dry the tissue as stated in e).
  g) Cut the washed pigskin into 1.7-2.0 cm*2.5 cm square samples with sterilized applicators. For each skin slice, put 3 pieces in one petri dish for one collection time.
  h) This step is operated in clean bench. Each pigskin slice cutting should be within 5 min. Avoid hand touch with pigskin. Sanitize the cutting applicator by 75% ethanol and allow sufficient ethanol evaporation in between pig skin slice.

1.3. Microbial Inoculation
  a) Bring the pigskin out from incubator to a clean bench. Inoculate 10 ul of the tested microorganism culture on each pigskin piece (1.7-2.0 cm*2.5 cm). Spread evenly over the pigskin surface with a sterile inoculation loop or pipette tip.
  b) Allow the inoculum to visually dry on the surface (approximately ~5-20 minutes) in clean bench.

1.4. Harvesting of Surviving Microorganisms after Residual Time
  a) Place tissues into humidified incubator at 35±2° C. and 60±20% RH until time of collection.
  b) At each sampling time, aseptically transfer each pigskin piece to 50 mL Modified Letheen Broth with Tween and Lecithin (MLBTL) in a sterile blue cap bottle.
  c) Shake the bottles containing the MLBTL and pigskin vigorously for 1 min.
  d) Perform serial dilutions using MLBTL. Prepare serial dilution by transferring 1ml wash solution to 9 ml MLBT or 0.5 ml wash solution to 4.5 ml diluent. Mix well by vortexing before further dilution and plating.

1.5. Plating, Incubation and Counting
  a) Aseptically pipette 0.5 ml or 1.0 ml of the dilution into each of two sterile petri dish, pour around 15 ml Modified Letheen Agar with Tween media into each petri dish and swirl the plate to mix the contents, once the agar has solidified, invert the plate and incubate at 35±2° C. for 18-24 hours.
  b) Calculate the microorganism density (CFU/ml) in 50 ml neutralizer from plate enumeration. Calculate LOG 10 (CFU/site) for all collection time points. CFU/ml= (plate1 count+plate2 count)/2*dilution factor LOG 10 CFU/site=LOG 10 (CFU/ml*50 ml/site)

Combinatorial Minimum Inhibitory Concentration (cMIC) Method

A Combinatorial Minimum Inhibitory Concentration ("cMIC") is used to determine the combinatorial effects of two chemicals on anti-bacterial activity in a tissue culture setting. Herein, the cMIC is a measure of the Minimum Inhibitory concentrations (MIC) of Hinokitiol in combination with Piroctone Olamine or vice versa.

1. Method Overview:
  a. Each cMIC assay is run in triplicates.
  b. *Staphylococcus aureus* ATCC 6538 is cultured on tryptic soy agar (TSA) (Oxoid CM0131) over 24 hours. The single colonies are then transferred into saline and mixed through vortex to obtain an optical density (OD) of 0.08-0.13 at 620 nm. 200 µL of this bacterial suspension is added to 19.8 mL of Mueller Hinton Broth (MHB) (BD 212322). This gives $5 \times 10^5$ cfu/mL. 100 µL of this bacteria-MHB mix is added to a 96 well flat-bottomed plate (TRP 92196).
  c. Hinokitiol is pipetted into the wells in varying concentrations as indicated below.
  d. Piroctone Olamine is pipetted into the wells in varying concentrations, as indicated below.
  e. The plates are then read using a spectrophotometer at 620 nm. This is the 0-hour reading.
  f. The plates are incubated at 37° C. between 18-24 hours with shaking at 50 rpm.
  g. The optical density of the plate is then measured using a spectrophotometer at 620 nm.
  h. The OD value is calculated as subtraction of the readings between 18-24 hour and the 0-hour.
  i. cMIC is determined as the minimal concentration of Hinokitiol in combination with Piroctone Olamine or vice versa, corresponding to the well whose OD value is less than 10% of the OD value of the control well without Hinokitiol and Piroctone Olamine (full growth).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rinse-off cleansing composition comprising a soap, a surfactant, or a combination thereof; hinokitiol; and piroctone olamine and wherein the ratio by weight of piroctone olamine to the hinokitiol is about 2:1 and the combination of piroctone olamine and hinokitiol comprise about 9 ppm or more by weight of the cleansing composition.

2. The rinse-off cleansing composition of claim 1, wherein the composition comprises from about 3 ppm to about 0.5%, by weight of the cleansing composition, of the hinokitiol.

3. The rinse-off cleansing composition of claim 1, wherein the composition comprises from about 6 ppm to about 1%, by weight of the cleansing composition, of the piroctone olamine.

4. The rinse-off cleansing composition of claim 1, wherein the composition is a bar soap.

5. The rinse-off cleansing composition of claim 4, wherein the composition comprises from about 65% to about 98%, by weight of the cleansing composition, of soap, a synthetic surfactant, or a combination thereof.

6. The rinse-off cleansing composition of claim 5, wherein the composition comprises from about 5% to about 30%, by weight of the composition, of a starch.

7. The rinse-off cleansing composition of claim 1, wherein the composition is a liquid cleansing composition.

8. The rinse-off cleansing composition of claim 1, wherein the level of piroctone olamine is about 3 ppm to about 25 ppm by weight of the composition.

9. The rinse-off cleansing composition of claim 1, wherein the level of hinokitiol is 3 ppm to about 50 ppm by weight of the composition.

10. A hand sanitizing composition, comprising an alcohol; hinokitiol; and piroctone olamine and wherein the ratio by weight of the piroctone olamine to the hinokitiol is to about 2:1 and the combination of the piroctone olamine and hinokitiol comprise about 9 ppm or more by weight of the cleansing composition.

11. The hand sanitizing composition of claim 10, wherein the hinokitiol is present at a level of about 3 ppm or more, by weight of the composition.

12. The hand sanitizing composition of claim 11, wherein the piroctone olamine is present at a level of about 6 ppm or more, by weight of the composition.

13. The hand sanitizing composition of claim 12, wherein the alcohol is present at a level of about 30% to about 80%, by weight of the hand sanitizing composition.

* * * * *